(12) United States Patent
Sato

(10) Patent No.: US 7,942,812 B2
(45) Date of Patent: May 17, 2011

(54) ENDOSCOPIC APPARATUS AND DIAGNOSIS SYSTEM

(75) Inventor: Yoshiaki Sato, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 1128 days.

(21) Appl. No.: 11/674,772

(22) Filed: Feb. 14, 2007

(65) Prior Publication Data

US 2007/0191680 A1    Aug. 16, 2007

(30) Foreign Application Priority Data

Feb. 14, 2006 (JP) .................. 2006-036411

(51) Int. Cl.
*A61B 1/00* (2006.01)
(52) U.S. Cl. ......... 600/118; 600/101; 600/103; 600/131
(58) Field of Classification Search .................. 600/101, 600/118, 103, 131; 378/190
See application file for complete search history.

(56) References Cited

U.S. PATENT DOCUMENTS

| | | | | |
|---|---|---|---|---|
| 4,993,404 A | * | 2/1991 | Lane | 600/109 |
| 5,127,394 A | * | 7/1992 | Lane | 600/112 |
| 5,605,531 A | * | 2/1997 | Lane et al. | 600/118 |
| 6,198,794 B1 | * | 3/2001 | Peshkin et al. | 378/42 |
| 6,368,269 B1 | * | 4/2002 | Lane | 600/126 |
| 2003/0181800 A1 | * | 9/2003 | Bonutti | 600/407 |
| 2006/0063973 A1 | * | 3/2006 | Makower et al. | 600/114 |
| 2006/0095066 A1 | * | 5/2006 | Chang et al. | 606/199 |

FOREIGN PATENT DOCUMENTS

| | | |
|---|---|---|
| JP | 2002-209885 A | 7/2002 |
| JP | 2004-344540 A | 12/2004 |

* cited by examiner

*Primary Examiner* — John P Leubecker

(74) *Attorney, Agent, or Firm* — Sughrue Mion, PLLC

(57) ABSTRACT

A diagnosis system composed of a fluoroscopic apparatus for obtaining a fluoroscopic image of an internal body be radiating x-rays to the body, and an endocopic apparatus for obtaining an optical image of the internal body part to be observed by inserting an insertion section of the endoscope into the body. In an operating section of the endoscope, a fluoroscope operating section for operating the fluoroscopic apparatus is disposed. Operation signals from the fluoroscope operating section are sent from a communication I/F of an endoscopic processor to the fluoroscopic apparatus. The fluoroscoptic apparatus receives the operation signals with a fluoroscopic processor and controls a fluoroscopic table.

8 Claims, 4 Drawing Sheets

US 7,942,812 B2

ENDOSCOPIC APPARATUS AND DIAGNOSIS SYSTEM

BACKGROUND OF THE INVENTION

1. Field of the Invention

The present invention relates to an endoscopic apparatus which obtains an endoscopic image with an endoscope, and a visual diagnosis system composed of this endoscopic apparatus and a fluoroscopic apparatus which obtains a fluoroscopic image using x-rays.

2. Description Related to the Prior Art

Medical diagnoses utilizing an endoscope have widely been practiced in the medical field these days. The endoscope has an insertion section that is introduced into a body. In a distal end of the elongated insertion section, an imaging section is located. The imaging section includes an imaging device like a CCD, which obtains an endoscopic image by capturing image light of an internal body part to be observed, a lens for collecting light into the imaging device, and an illumination window for releasing illumination light. In the distal end of the insertion section, a forceps opening is also formed. Through this opening, forceps, which are surgical instruments for pressing organs, tissues and the like by nipping or firmly holding them, go in and out.

The insertion section is tubular and flexible, and holds an optical fiber for transmitting the illumination light to the illumination window, wires for moving the forceps and for bending the insertion section so as to change a capturing angle of the imaging section, and the like. A grip for holding the endoscope is provided at a base end of the insertion section. An operating member for directing image capture and for changing the capturing angle is provided at the grip. An operates the operating member with one hand while holding the grip with the other hand to support the insertion section.

Endoscopic Retrograde Cholangio-Pancreatography (ERCP) is known as one of the medical diagnosis methods using such endoscope. ERCP is a procedure for injecting a contrast agent form the endoscope into a biliary tract or a pancreatic duct, and capturing images of such areas using an x-ray fluoroscopic apparatus. In order to inject the contrast agent, the distal end of the insertion section is firstly inserted into a duodenum. A cannula is then introduced through the forceps opening, and selectively inserted into the biliary tract or the pancreatic duct from a duodenal major papilla to inject the contrast agent. Since the contrast agent is injected against the flow of bile or pancreatic juice, the injection volume and the injection pressure of the contrast agent need to be carefully controlled. Moreover, the operator has to capture images with precise timing while observing not only a monitor of the endoscopic apparatus but also a monitor of the x-ray fluoroscopic apparatus.

As known, the x-ray fluoroscopic apparatus radiates x-rays on a body. By detecting the x-rays passed through the body, the internal body image can be obtained (see Japanese Laid-open Patent Publication Nos. 2002-209885 and 2004-344540). The x-ray fluoroscopic apparatus has a fluoroscopic table composed of a patient table and a fluoroscope imaging section. The fluoroscope imaging section is composed of an x-ray tube for radiating x-rays, and a detector disposed opposite the x-ray tube to detect the x-rays. When the fluoroscope imaging section and the patient table are moved by operating a console, object distance and image capture position are changed.

Since the endoscopic apparatus and the x-ray fluoroscopic apparatus are operated by different operator in ERCP conventionally, a lot of people have to engage in the diagnosis.

SUMMARY OF THE INVENTION

An object of the present invention is to provide an endoscopic apparatus and a diagnosis system that requires fewer people to perform a diagnosis using both of the endoscopic apparatus and an x-ray fluoroscopic apparatus.

To achieve the above and other objects, an endoscopic apparatus of the present invention includes an endoscope whose insertion section is introduced into a body and has an imaging device which captures image light of an internal body part to be observed to output an image signal, a processor having an endoscopic image producer for producing an endoscopic image from the image signal, at least one fluoroscope operating section and a transmitter. The fluoroscope operating section operates a fluoroscopic apparatus that looks through the body be radiating x-ray to the body. The transmitter is provided in the processor, and sends an operation signal from the fluoroscope operating section to the fluoroscopic apparatus.

The fluoroscope operating section is preferably disposed in the endoscope. The fluoroscope operating section is preferably located in an endoscope operating section used for operating the endoscope. The endoscope operating section is disposed at a base end of the insertion section of the endoscope.

The fluoroscope operating section may be disposed in the processor. At this time, the fluoroscope operating section is preferably a console that is connected to the processor. It is also possible to dispose the fluoroscope operating section in each of the endoscope and the processor.

The fluoroscopic apparatus preferably includes a fluoroscoptic table composed of a fluoroscope imaging section for capturing a fluoroscopic image and a patient table on which the body is laid. The fluoroscope operating section controls posture. of the patent table and an image capture position of the fluoroscope imaging section.

A visual diagnosis system of the present invention includes an endoscopic apparatus and a fluoroscopic apparatus. The endoscopic apparatus includes an endoscope having an insertion section and an imaging device located at an end of the insertion section. The insertion section is introduced into a body to captures an image of an internal body part to be observed. The fluoroscope apparatus looks through the body by radiating x-rays to the body. In the endoscopic apparatus, at least one fluoroscope operating section for operating the fluoroscopic apparatus and a transmitter for sending an operation signal from the fluoroscope operating section to the fluoroscopic apparatus are disposed. In the fluoroscopic apparatus, a receiver for receiving the operation signal and a controller for controlling the fluoroscopic apparatus based on the operation signal are disposed.

The endoscopic apparatus is preferably composed of the endoscope and a processor having an endoscopic image producer for producing an endoscopic image from an image signal output from the imaging device. The fluoroscope operating section is disposed in the endoscope and/or the processor.

According to the present invention, the endoscope incorporates the fluoroscope operating section and the transmitter which sends the operation signal from the fluoroscope operating section to the fluoroscopic apparatus. Owing to this, the medical diagnosis using both of the endoscopic apparatus and the fluoroscopic apparatus can be performed by fewer people.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein.

DESCRIPTION OF THE PREFERRED EMBODIMENTS

Figure 1:
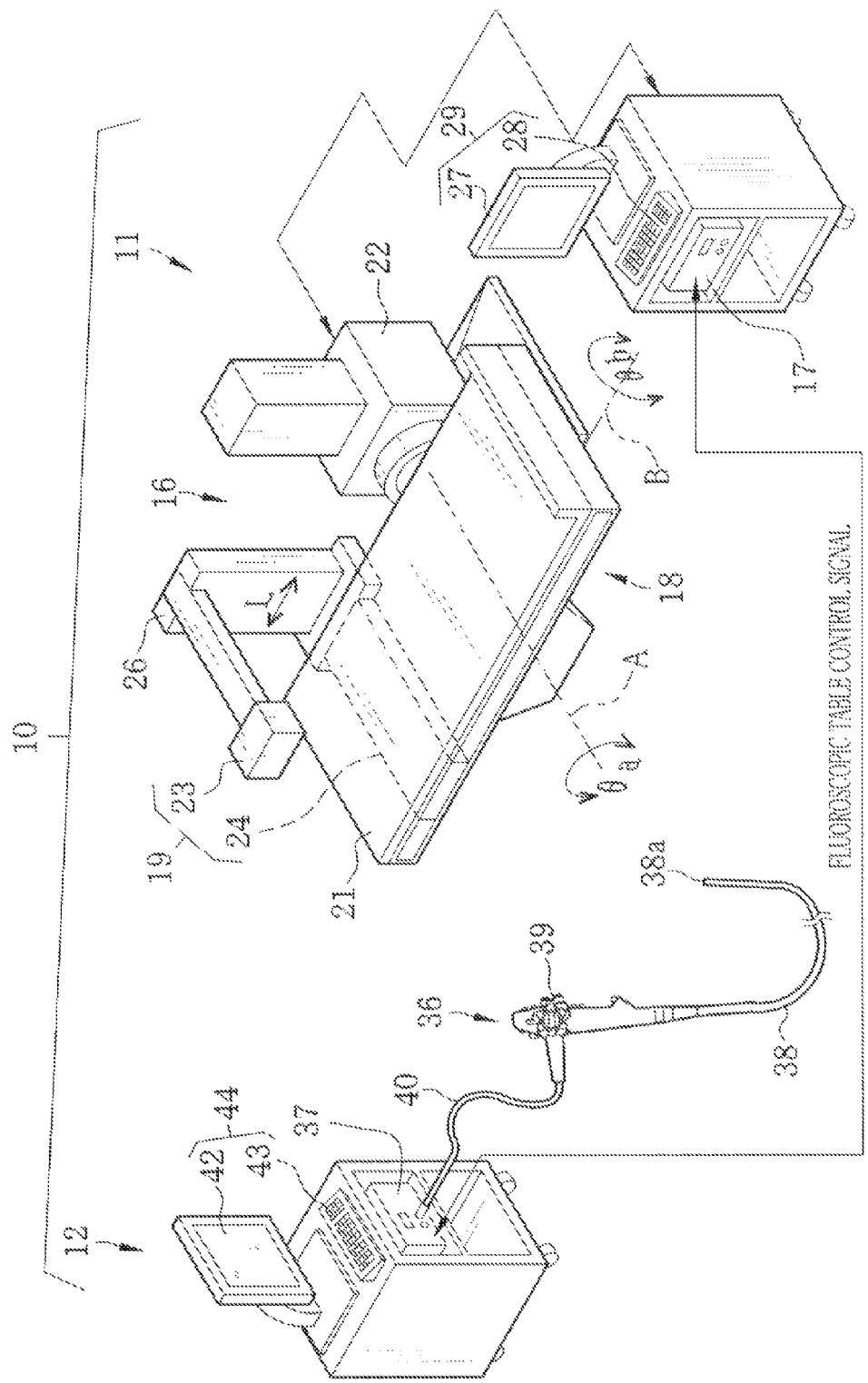
FIG. 1 is a block diagram illustrating a diagnosis system of the present invention.

FIG. 1 shows a diagnosis system 10 composed of an x-ray fluoroscopic apparatus (hereinafter, fluoroscopic apparatus) 11 and an endoscopic apparatus 12. The diagnosis system 10 is used for diagnoses using both the fluoroscoptic apparatus 11 and the endoscopic apparatus 12 like ERCP. The fluoroscopic apparatus 11 is composed of a fluoroscopic table 16 and a fluoroscopic processor 17.

The fluoroscopic table 16 includes a patient table 18 on which a patient is laid, and a fluoroscope imaging section 19 for capturing a fluoroscopic image by radiating x-rays to the patient on the patient table 18. The patient table 18 is composed of a plate 21 and a posture control mechanism 22 for supporting the plate 21 and changing posture of the plate 21. The posture control mechanism 22 rotates the plate 21 around axes A and B (shown with chain double-dashed lines) to change its posture.

The fluoroscope imaging section 19 is composed of an x-ray tube 23 for applying x-ray and a flat panel detector (FPD) 24 for detecting the x-ray passed through the patient's body so as to output a detection signal as a fluoroscopic image signal. The x-ray tube 23 is located above the plate 21 and the FPD 24 are connected with each other through a substantially L-shaped support arm 26. The FPD 24 is mounted to move along a longitudinal direction (L-direction) of the plate 21. When the FPD 24 moves, relative position of the patient and the x-ray tube 23 changes, and thereby an image capture position of the fluoroscope imaging section 19 is changed.

the fluoroscopic processor 17 produces the fluoroscopic image based on the fluoroscopic image signal output from the FPD 24. A console 29 composed of a monitor 27 and a key board 28 is connected to the fluoroscopic processor 17. The monitor 27 displays an operation screen as sell as the fluoroscopic image produced by the fluoroscopic processor 17. In addition, the fluoroscopic processor 17 controls the fluoroscopic table 16 based on operation signals input from the key board 28 according to the operation screen.

The endoscopic apparatus 12 is composed of an endoscope 36 and an endoscopic processor 37. The endoscope 36 has an insertion section 38 that is introduced into a body cavity, and an operating section 39 that is connected to a base end of the insertion section 38. In a front end section 38a leading from a distal end of the insertion section 38, an objective lens for taking in image light of a part to be observed in the body cavity, a CCD 59 (see FIG. 4) as an imaging device for capturing an image of the part to be observed in the body cavity, an illumination window for releasing illumination light, a forceps opening for letting forceps in and out and nozzles for sending water and air so as to clean up the lens are disposed.

Inside the insertion section 38, an angle wire for changing a capturing angle of the CCD 59, a light guide composed of an optical fiber for transmitting the illumination light from a light source 52 (see FIG. 4) to the illumination window, a signal cable for transmitting the image signal from the CCD 59 or the operation signals for directing image capture and the like, a water supply pipe, an air supply pipe, and the like are inserted therethrough. Behind the front end section 38a, joint pieces constituting a flexible section are disposed. When the angle wire is pushed or pulled by operating the operating section 39, the front end section 38a curves to the right, left, up and down, and thereby directing the capturing angle to a desired direction.

The endoscope 36 is connected to the endoscopic processor 37 through a cord 40. The endoscopic processor 37 applies image processing to the image signal output from the CCD 59, and produces an endoscopic image. A console 44 composed of a monitor 42 and a key board 43 is connected to the endoscopic processor 37. The monitor 42 displays an operation screen as well as the endoscopic image produced by the endoscopic processor 37. The endoscopic processor 37 is controlled based on operation signals input from the key board 43 according to the operation screen.

Figure 2:
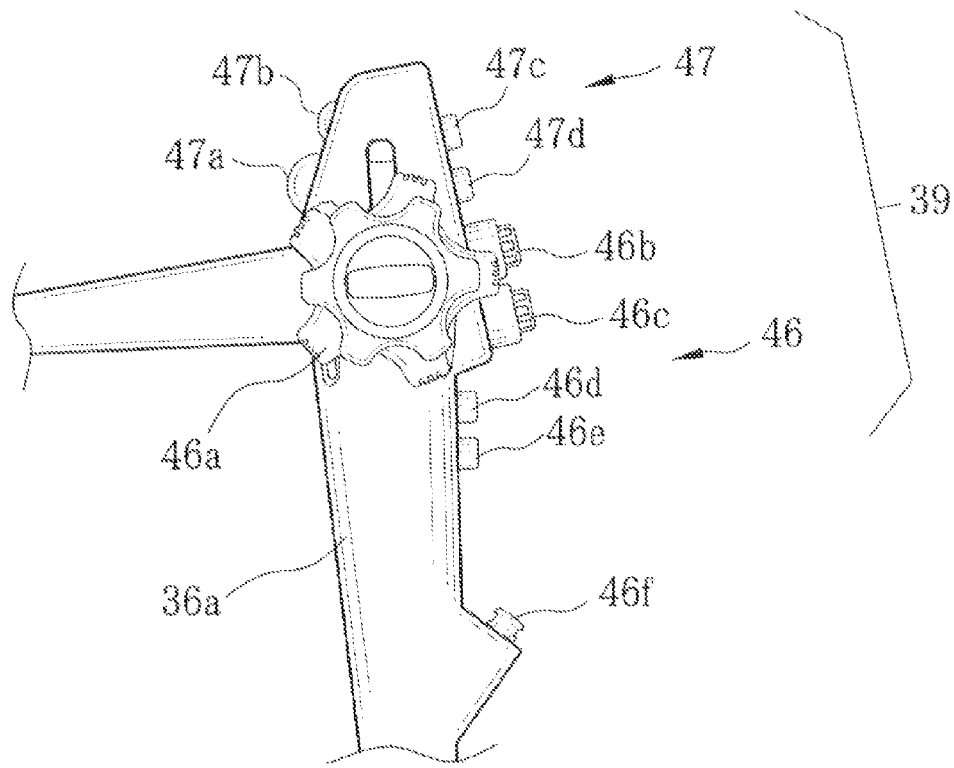
FIG. 2 is an explanatory view illustrating an operating section of an endoscope.

As shown in FIG. 2, the operating section 39 of the endoscope 36 has a fluoroscope operating section 47 for operating the fluoroscopic apparatus 11, as well as an endoscope operating section 46 composed of operating members for operating the endoscope 36. For this configuration, the operator of the endoscope 36 can also operate the fluoroscopic apparatus 11 through the operating section 39.

The endoscope operating section 46 is composed of, for example, an angle knob 46a for pushing or pulling the angle wire to change the capturing angle, a water supply button 46b for supplying water, an air supply button 46c for supplying are, and display switchover buttons 46d and 46e. The display switchover buttons 46d and 46e switch between a live display and a freeze display. The live display sequentially shows a plurality of frames, which are obtained with the CCD 59 at a predetermined frame rate, on the monitor 42 in real time. The freeze display shows one frame of a still image by freezing the update of the displayed frame. When the button 46d is depressed, the live display is selected, and when the button 46d is depressed, the freeze display is selected. The numeral 46f indicates a forceps insertion opening for inserting the forceps.

The fluoroscope operating section 47 is composed of a plate operating member 47a for changing the posture of the plate 21, an imaging section operating member 47b for moving the fluoroscope imaging section 19, and display switchover buttons 47c and 47d for switching the display of the fluoroscope imaging section 19. The display switchover buttons 47c and 47d switch between the live display and the freeze display of the fluoroscopic image obtained with the fluoroscope imaging section 19 on the monitor 27. When the button 47c is depressed, the live display is selected, and when the button 47d is depressed, the freeze display is selected. In many cases, the endoscope operator holds a grip 36a of the endoscope 36 with one hand, and operates the operating section 39 with the same hand. Therefore, the fluoroscope operating section 47 is located in such a position where the operator can easily operate it with one hand.

Figure 3:
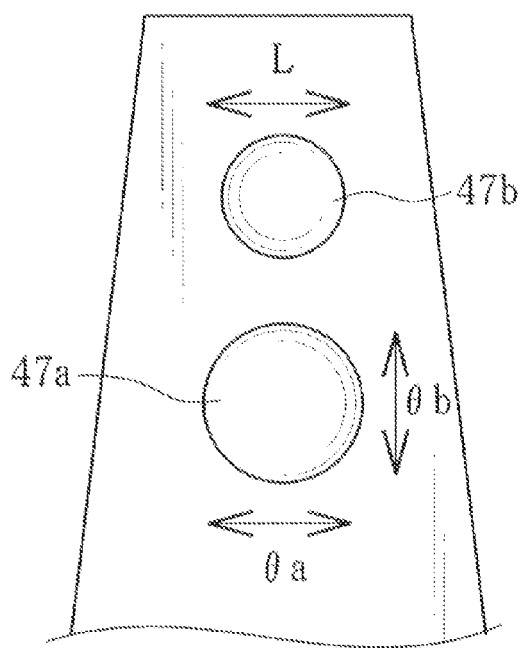
FIG. 3 is an explanatory view illustrating a fluoroscope operating section.

As shown in FIG. 3, the plate operating member 47a and the imaging section operating member 47b are trackballs. When each rotatably mounted ball is rotated, the operating members 47a and 47b input operating signals. The plate operating member 47a rotates in, for example, longitudinal and horizontal directions perpendicular to each other. One direction corresponds to θa-direction centered on the axis A (see FIG. 1), and the other direction corresponds to θb-direction centered on the axis B (see FIG. 1). The imaging section operating member 47b rotates in the horizontal direction which corresponds to the L-direction of the fluoroscope imaging section 19. Rotation direction and rotation amount of the plate operating member 47a and the imaging section operating member 47b are detected by a rotary encoder or the like, and input as the operating signals.

Figure 4:
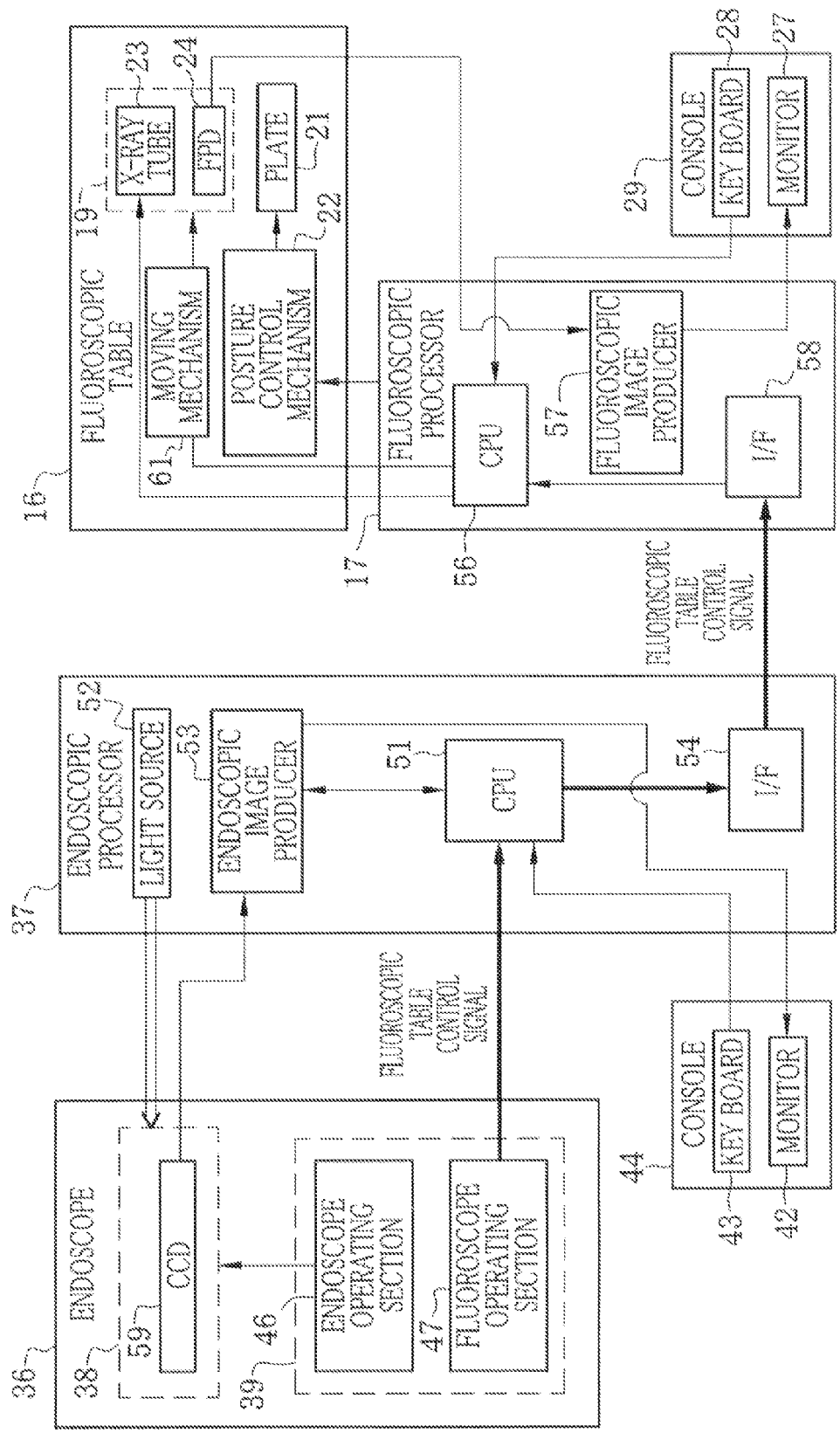
FIG. 4 is a block diagram illustrating a structure of the diagnosis system.

As shown in FIG. 4, a CPU 51, the light source 52 for emanating the illumination light, an endoscopic image producer 53 and a communication I/F 54 are disposed in the endoscopic processor 37 of the endoscopic apparatus 12. The CPU 51 takes overall control of the endoscopic processor 37. The illumination light from the light source 52 is transmitted to the illumination window through the light guide of the endoscope 36. In the present embodiment, the light source 52 is disposed in the endoscopic processor 37 and the illumination light is guided to the front end section 38a of the insertion section 38 through the light guide. However, the light source like LED may be provided in the front end section 38a. For this configuration, the light guide is not necessary.

The endoscopic image producer 53 applies image processing to the image signal output from the CCD 59, and produces the endoscopic image. The endoscopic image is output to the monitor 42. The communication I/F 54 is an external device communicating section that controls the communication with the external devices. The communication I/F 54 receives a fluoroscopic table control signal input from the fluoroscope operating section 47 disposed in the endoscope 36 and sends it to the fluoroscopic processor 17.

A CPU 56, a fluoroscopic image producer 57 and a communication I/F 58 are disposed in the fluoroscopic processor 17. The CPU 56 takes overall control of the fluoroscopic processor 17, the controls the fluoroscopic table 16 based on the operation signals from the console 29 or based on the fluoroscopic table control signal sent from the encoscopic apparatus 12. The fluoroscopic image producer 57 applies image processing to the fluoroscopic image signal output from the FPD 24, and produces the fluoroscopic image. This fluoroscopic image is output to the monitor 27. The communication I/F 58 is an external device communication section that controls the communication with the external devices. The communication I/F 58 receives the fluoroscopic table control signal from the communication I/F 54 of the endoscopic apparatus 12. The received fluoroscopic table control signal is input to the CPU 56. Wired communication is established between the communication I/F 54 and 58, but the communication can be, of course, established wirelessly.

In addition to the posture control mechanism 22 for driving the plate 21, a moving mechanism 61 for driving the fluoroscope imaging section 19 is disposed in the fluoroscopic table 16. The CPU 56 controls the posture control mechanism 22 based on the operation signals input from the console 29, and the moving mechanism 61 based on the operation signals input from the endoscopic apparatus 12.

Hereinafter, operation of the diagnosis system having the above configuration is explained. When ERCP is performed, the patient is laid on the plate 21, and the insertion section 38 of the endoscope 36 is inserted into the body. The operator of the endoscope 36 operates the operating section 39 with one hand while holding the grip 36a with the same hand to support the insertion section 38. The operation is executed while the monitor 42 of the endoscopic apparatus 12 and the monitor 27 of the fluoroscopic apparatus 11 are observed. The operator can operate not only the endoscope 36 but also the fluoroscopic table 16 from the operating section 39. Since the endoscope operator can capture the fluoroscopic images, the diagnosis can be performed with fewer people than the conventional method.

Figure 5:
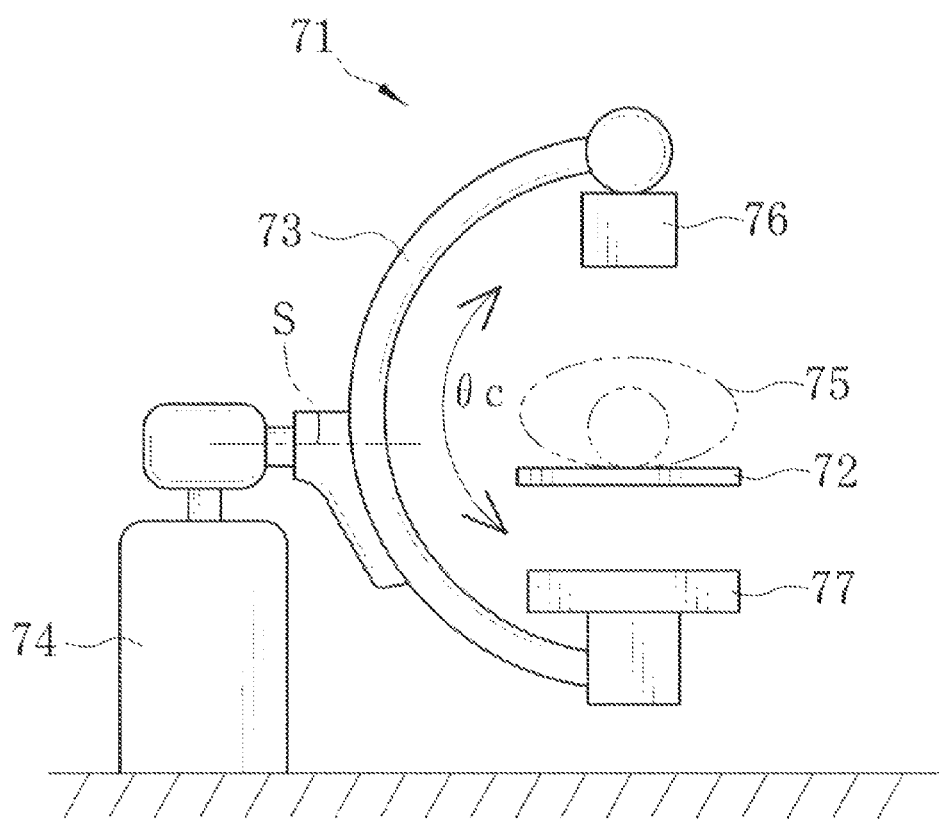
FIG. 5 is an explanatory view illustrating a fluoroscoptic table having a C-shaped arm.

In the above embodiment, the fluoroscopic table having the fluoroscope imaging section, which moves along the longitudinal direction of the plate, is explained as an example. However, a fluoroscopic table 71 having a C-shaped arm 73 shown in FIG. 5 may be used. In the fluoroscopic table 71, the C-shaped arm 73 is formed such that its open ends are each located above and below a plate 72, on which a patient 75 is laid, to interpose the plate 72 therebetween. The C-shaped arm 73 is mounted to a base 74 and swings in θc direction along its circular contour. The C-shaped arm 73 is also rotatable about an axis S. One of the open ends of the C-shaped arm 73 is provided with an x-ray tube 76 and the other is provided with an FPD 77. The x-ray tube 76 and the FPD 77 constitute the fluoroscope imaging section. When the C-shaped arm 73 rotates or swings, the relative position of the fluoroscope imaging section to the plate 72 changes, and thereby a capturing angle is changed. The endoscope 36 may be provided with, for example, an operating member having the above-mentioned trackball configuration. The C-shaped arm 73 may be controlled by this operating member.

In the above embodiments, the trackball is explained as the operating member in the fluoroscope operating section. However, the operating member may be, for example, a trackpad of a set of switches. The trackpad inputs operation signals by detecting movements of fingers on the flat pad electrostatically or pressure-sensitively. The set of switches corresponds to the moving directions, and the fluoroscopic table can be moved in the direction that the depressed switch corresponds.

In the above embodiments, the fluoroscope operating section is disposed in the operating section of the endoscope. However, the fluoroscopic table may be operated from the console connected to the endoscopic processor, or may be operated from both of the endoscope and the endoscopic processor. In addition, foot switches or foot pedals may be used as the fluoroscope operating section. The foot switches or pedals are connected to the endoscopic processor as well as the console.

In the above embodiments, the endoscope is equipped with the imaging device, which captures the optical image of the internal body part to be observed. However, the endoscope may also be equipped with ultrasonic transducers in addition to the imaging device. When the ultrasonic endoscope is used, the internal body part to be observed is irradiated with ultrasonic waves, and the ultrasonic transducers receive echo signals from the irradiated part. In this case, an ultrasonic image producer for producing an ultrasonic image from the echo signals is provided in the endoscopic processor.

Although the present invention has been described with respect to the preferred embodiments, the present invention is not to be limited to the above embodiments. On the contrary, various modifications will be possible without departing from the scope of claims appended hereto.

What is claimed is:

1. An endoscopic apparatus including an endoscope whose insertion section is introduced into a body and has an imaging device which captures image light of an internal body part to be observed to output an image signal, and a processor having an endoscopic image producer for producing an endoscopic image from said image signal, said endoscopic apparatus comprising:

at least one fluoroscope operating section for operating a fluoroscopic apparatus, said fluoroscopic apparatus looking through said body by radiating x-ray to said body;

a transmitter provided in said processor, for sending an operation signal from said fluoroscope operating section to said fluoroscopic apparatus; and wherein said fluoroscope operating section is disposed in said endoscope.

2. An endoscopic apparatus as claimed in claim 1, wherein said fluoroscope operating section is located in an endoscope operating section disposed at a base end of said insertion section and used for operating said endoscope.

3. An endoscopic apparatus as claimed in claim 1, wherein said fluoroscope operating section is disposed in said processor.

4. An endoscopic apparatus as claimed in claim 3, wherein said fluoroscope operating section is a console being connected to said processor.

5. An endoscopic apparatus as claimed in claim 1, wherein said fluoroscope operating section is disposed in each of said endoscope and said processor.

6. An endoscopic apparatus as claimed in claim 1, wherein said fluoroscopic apparatus includes a fluoroscopic table composed of a fluoroscope imaging section for capturing a fluoroscopic image and a patient table on which said body is laid, said fluoroscope operating section controlling posture of said patient table and an image capture position of said fluoroscope imaging section.

7. A system for a visual diagnosis, comprising:

an endoscopic apparatus including an endoscope having an insertion section and an imaging device located at an end of said insertion section, said insertion section being introduced into a body to capture an image of an internal body part to be observed; and a fluoroscopic apparatus for looking through said body by radiating x-rays to said body; wherein, said endoscope apparatus has at least one fluoroscope operating section for operating said fluoroscopic apparatus and a transmitter for sending an operating signal form said fluoroscope operating section to said fluoroscopic apparatus, said fluoroscopic apparatus has a receiver for receiving said operation signal and a controller for controlling said fluoroscopic apparatus based on said operation signal, and wherein said fluoroscope operating section is disposed in said endoscope.

8. A system as claimed in claim 7, wherein said endoscopic apparatus is composed of said endoscope and a processor having an endoscope image producer for producing an endoscopic image from an image signal output from said imaging device, and said fluoroscope operating section is disposed in said endoscope and/or said processor.

\* \* \* \* \*